(12) United States Patent
Skender et al.

(10) Patent No.: US 11,259,944 B2
(45) Date of Patent: Mar. 1, 2022

(54) STENT DEPLOYMENT SYSTEM WITH UNWRAPPING DEPLOYMENT CONSTRAINT

(71) Applicant: Cook Medical Technologies LLC, Bloomington, IN (US)

(72) Inventors: Davorin Skender, Bloomington, IN (US); Ralf Spindler, Solsberry, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 184 days.

(21) Appl. No.: 16/454,518

(22) Filed: Jun. 27, 2019

(65) Prior Publication Data

US 2020/0405519 A1    Dec. 31, 2020

(51) Int. Cl.
*A61F 2/962* (2013.01)
*A61F 2/954* (2013.01)
*A61F 2/966* (2013.01)

(52) U.S. Cl.
CPC .............. *A61F 2/962* (2013.01); *A61F 2/954* (2013.01); *A61F 2/9661* (2020.05); *A61F 2230/0091* (2013.01)

(58) Field of Classification Search
CPC .. A61F 2/95; A61F 2/962; A61F 2/954; A61F 2/966; A61F 2/97; A61F 2002/9623; A61M 25/0668; A61M 2025/0675; A61M 2025/1081; A61M 2025/0034
See application file for complete search history.

(56) References Cited

U.S. PATENT DOCUMENTS

| | | | |
|---|---|---|---|
| 5,948,191 A | 9/1999 | Solovay | |
| 6,224,627 B1 * | 5/2001 | Armstrong | A61F 2/82 623/1.13 |
| 6,350,278 B1 | 2/2002 | Lenker et al. | |
| 6,364,904 B1 | 4/2002 | Smith | |
| 6,827,731 B2 * | 12/2004 | Armstrong | A61F 2/97 623/1.12 |
| 6,939,327 B2 | 9/2005 | Hall et al. | |
| 7,384,428 B2 | 6/2008 | Richter | |
| 8,088,154 B2 | 1/2012 | Hoffman et al. | |
| 8,657,789 B2 | 2/2014 | Guo et al. | |
| 8,845,712 B2 | 9/2014 | Irwin et al. | |
| 8,915,951 B2 | 12/2014 | Weber | |
| 9,539,411 B2 * | 1/2017 | Cully | A61M 25/0668 |

(Continued)

FOREIGN PATENT DOCUMENTS

WO    2016196362    8/2016

*Primary Examiner* — Elizabeth Houston
*Assistant Examiner* — Uyen N Vo
(74) *Attorney, Agent, or Firm* — Liell & McNeil

(57) ABSTRACT

A stent delivery system includes a self expanding stent positioned about a distal support segment of a catheter, which includes a proximal segment. A constraint has a wrapped configuration, which has a hollow elongated shape, and an unwrapped configuration, which is a continuous length of a strip. The stent is in contact with, and held in a compressed state by, the constraint in the wrapped configuration, and the stent is in an expanded state out of contact with the constraint in the unwrapped configuration. The constraint may move from the wrapped configuration toward the unwrapped configuration responsive to tension in a control line connected to one end of the strip.

6 Claims, 4 Drawing Sheets

(56) References Cited

U.S. PATENT DOCUMENTS

| | | | |
|---|---|---|---|
| 2008/0255580 A1* | 10/2008 | Hoffman | A61F 2/95 606/108 |
| 2009/0182411 A1* | 7/2009 | Irwin | A61F 2/97 623/1.12 |
| 2009/0204196 A1* | 8/2009 | Weber | A61F 2/97 623/1.2 |
| 2009/0287292 A1* | 11/2009 | Becking | A61F 2/97 623/1.11 |
| 2014/0066898 A1* | 3/2014 | Cully | A61L 29/146 604/509 |
| 2015/0190257 A1 | 7/2015 | Cragg et al. | |
| 2015/0250630 A1* | 9/2015 | Irwin | A61F 2/9525 606/108 |

* cited by examiner

STENT DEPLOYMENT SYSTEM WITH UNWRAPPING DEPLOYMENT CONSTRAINT

TECHNICAL FIELD

The present disclosure relates generally to self-expanding stent delivery systems, and more particularly to a constraint that unwraps to deploy the stent.

BACKGROUND

An accurate and consistent ability to position a stent in the anatomy is one of the most important actions during a procedure. In many cases, self-expanding stents and stent grafts have been sheathed to constrain the stent for delivery, positioning and deployment. Deployment occurs from the distal end down by requiring the sheath to be pulled or retracted back in the direction of the clinician. This action may cause friction along the length of the stent, and additional force may be required from the clinician to complete deployment of the device. This additional friction for deployment can sometimes cause the device to move from an original alignment away from a location desired by the clinician. This added force also has the potential for significant misalignment and can lead to additional procedure time, fluoro time and contrast burden, and possible additional devices to fix misalignments, all adding risk to less than ideal outcomes.

During packing, the stent graft can be contorted so that flaps of material are formed in an uncontrolled manner, and features of the stent graft are touching where they should not. This distortion of the device's geometry has clinical evidence whereby clinicians will sometimes measure the device on the patient's belly prior to use, and the length will sometimes not match the label length of the device. In some instances, the stent graft may elongate during deployment and cause the clinician to have to adapt to the new length, and maybe do undesirable adjustments to prevent coverage of branch vessels. Uncontrolled folds in graft material can also disrupt blood flow.

The present disclosure is directed toward one or more of the problems set forth above.

SUMMARY

In one aspect, a stent delivery system includes a catheter that defines an axis, and has a distal support segment and a proximal segment. A self expanding stent is positioned about the distal support segment. A constraint has a wrapped configuration, which has a hollow elongated shape, and an unwrapped configuration, which is a continuous length of a strip. The stent is in contact with, and held in a compressed state by, the constraint in the wrapped configuration, and the stent is in an expanded state out of contact with the constraint in the unwrapped configuration. The constraint includes the strip wrapped onto itself in a plurality of layers in the wrapped configuration.

In another aspect, a stent delivery system includes a catheter that defines an axis, and has a distal support segment and a proximal segment. A self expanding stent is positioned about the distal support segment. A constraint has a wrapped configuration, which has a hollow elongated shape, and an unwrapped configuration, which is a continuous length of a strip. The stent is in contact with, and held in a compressed state by, the constraint in the wrapped configuration, and the stent is in an expanded state out of contact with the constraint in the unwrapped configuration. The constraint unwraps from a distal end toward a proximal end of the distal support segment when changing from the wrapped configuration to the unwrapped configuration.

In another aspect, a stent delivery system includes a catheter that defines an axis, and has a distal support segment and a proximal segment. A self expanding stent is positioned about the distal support segment. A constraint has a wrapped configuration, which has a hollow elongated shape, and an unwrapped configuration which is a continuous length of a strip. The stent is in contact with, and held in a compressed state by, the constraint in the wrapped configuration, and the stent is in an expanded state out of contact with the constraint in the unwrapped configuration. The constraint unwraps from a proximal end toward a distal end of the distal support segment when changing from the wrapped configuration to the unwrapped configuration. A portion of the strip moves in a proximal direction along the axis through the stent responsive to the constraint changing from the wrapped configuration toward the unwrapped configuration.

DETAILED DESCRIPTION

Those with skill in the art are familiar with delivery systems for self expanding stents. Most of these stent delivery systems include a catheter with a distal support segment and a proximal segment, and a self expanding stent is positioned about the distal support segment. A retractable sheath holds the stent in a compressed state while the delivery system is maneuvered within a patient to an implantation site. Thereafter, the retractable sheath is withdrawn to allow the stent to transition from its compressed state to an expanded state. Rather than dragging a sheath along the stent during the delivery procedure, the present disclosure substitutes a constraint in place of the retractable sheath associated with stent delivery systems of the prior art. The constraint transitions from a wrapped configuration to an unwrapped configuration to allow the stent to self expand from a compressed state to an expanded state. The ability to slowly and controllably unwrap the constraint can help avoid some undesirable phenomena associated with retractable sheaths, including but not limited to unpredictable position jumping during stent deployment.

Figure 1:
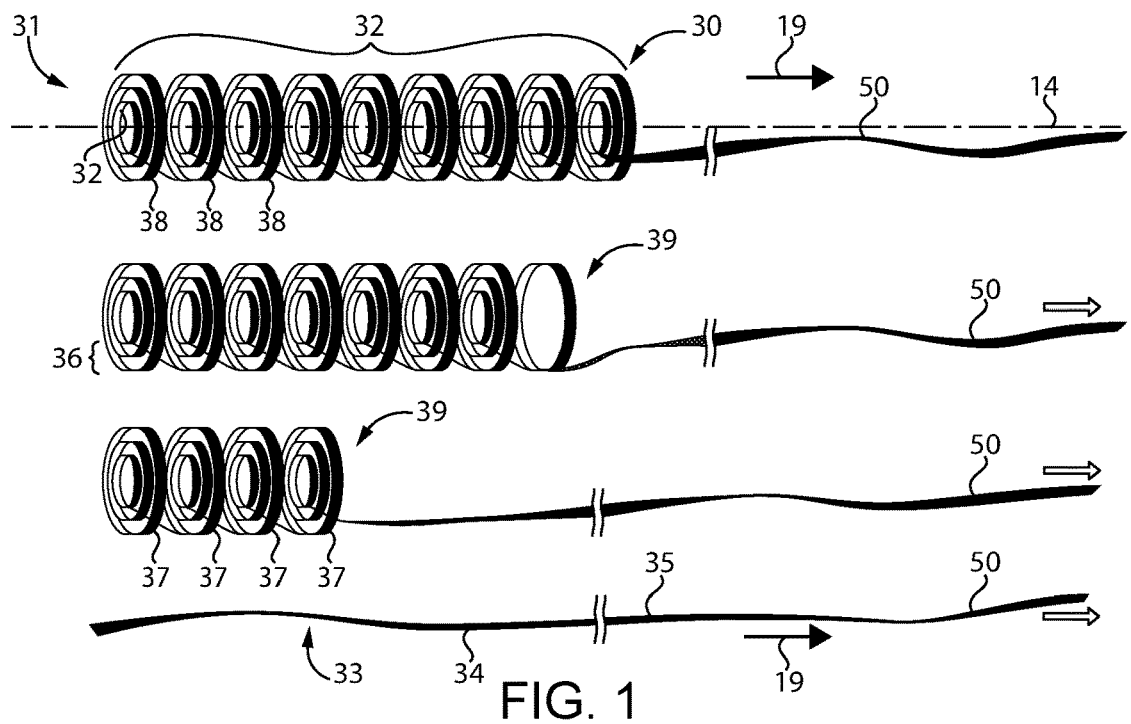
FIG. 1 is a schematic sequence of views showing a constraint according to the present disclosure changing from a wrapped configuration to an unwrapped configuration.
Figure 2:
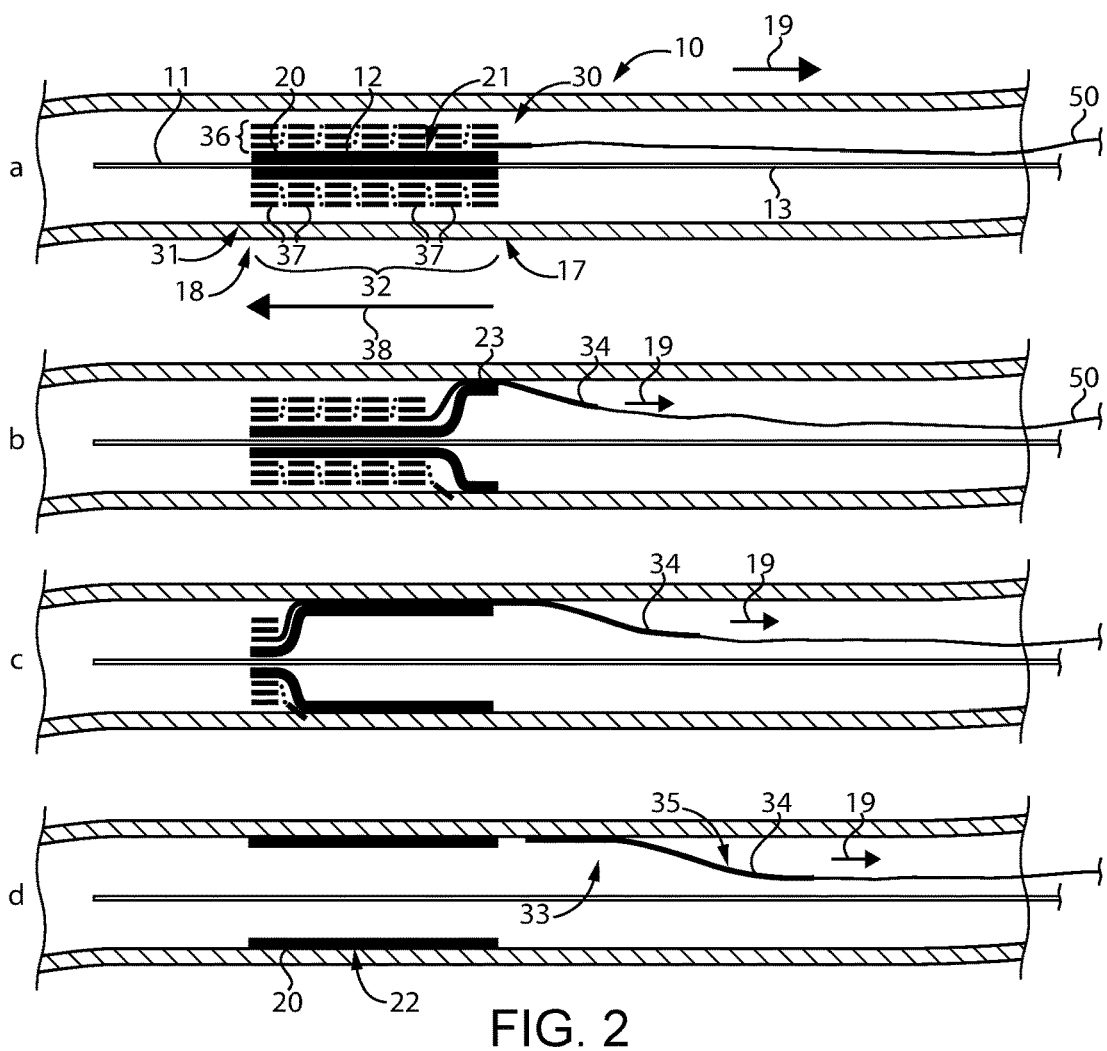
FIG. 2 is a sequence of views showing a stent delivery system deploying a stent according to the present disclosure.

Referring initially to FIGS. 1 and 2, a constraint 30 according to one aspect of the present disclosure is shown transitioning from a wrapped configuration 31 through two partially wrapped configurations 39 and eventually to an unwrapped configuration 33, in isolation from other features of a stent delivery system 10, respectively. Constraint 30 has a hollow elongated shape 32 in the wrapped configuration, and changes to a continuous length 35 of a strip 34 in the unwrapped configuration 33. According to the present disclosure, a "strip" has a cross sectional shape, resembling a ribbon or tape, capable of wrapping onto itself and stably remaining in a wrapped configuration until actively unwrapped. Thus, a strip according to the present disclosure is not a wire with a circular or oval cross section, but may be a thin strip of (PTFE) polytetrafluoroethylene with a cross sectional width that is always greater, and may be an order of magnitude or more greater, than a thickness dimension. In most instances, a strip according to the present disclosure will have a uniform cross section along its entire length, but a cross section that includes some dimensional variations could also fall within the intended scope of the present disclosure. Those skilled in the art will appreciate that it may be desirable to make the strip as thin as possible while retaining sufficient tensile strength to avoid breaking while in tension and while undergoing other stresses during a deployment procedure. While a strip according to the present disclosure could be formed from a single material, such as PTFE or another low surface energy material, the strip may be reinforced for added tensile strength, such as maybe by embedding nanotube based fibers into a composite strip of two or more materials. PTFE may be preferred because of its low surface energy, as the strip will likely slide along various surfaces, including possibly an interior or exterior surface of a stent graft, suggesting that a low friction material may be desirable. Nevertheless, other plastics, or may be even a metal strip, could still be strips according to the present disclosure. A strip according to the present disclosure also preferably has the ability to fold along lines perpendicular to its width dimension so that the unwrapped portion of the strip may pass through smaller openings, portals, or channels in the stent delivery system. For instance, a strip according to the present disclosure may have a width dimension that is greater than a catheter lumen diameter for the stent delivery system, while the strips ability to fold across its width dimension still allows the strip to be maneuvered along the catheter lumen.

The constraint 30 of FIGS. 1 and 2 differs from those described infra in that the strip 34 is wrapped onto itself in a plurality of layers 36 in the wrapped configuration. For illustrative purposes only, the number of layers is shown as being three in this example embodiment. Nevertheless, the present disclosure contemplates a range of a number of layers that could be between two and twenty five, with three to ten layers being a preferred number. The exact number of wrapping layers may depend on the specific application and the project scope. This may define the French size sheath (ID and OD), the material selection, the layer thickness, the thickness of a possible optional securement layer, and the tensile strength of the strip during the unwrapping deployment. All these parameters may contribute to fulfill the design requirements for a particular application. During manufacture, the layer wrapping could be created on a mandrel, and could be pushed over a compressed stent in a traditional manner as in sheaths of the prior art. Alternatively, a crimped stent may be kept in a crimped condition such as by using low temperatures and slid into the constraint at time of manufacture.

The constraint 30 of FIGS. 1 and 2 includes a plurality of coils 37 arranged in a series 38 along an axis 14, which may be defined by an underlying catheter 11 (not shown in FIG. 1). Each of the coils 37 includes the strip 34 wrapped onto itself in a plurality of layers 36 (three layers in the illustrated example) in the wrapped configuration 31. Each of the coils 37 may have a width on the order of the width of the strip 34, and the series 38 of coils may combine to define the hollow elongated cylindrical shape 32 that has a length that is many times the width of strip 34. For instance, the strip may have a width on the order of one to several millimeters, and the hollow elongate shape 32 may have a length of maybe one to ten centimeters or more. Thus, the length of hollow elongated shape may be at least one order of magnitude greater than the strip width. As illustrated, the coils 37 sequentially unwrap responsive to the constraint 30 changing from the wrapped configuration 31 to the unwrapped configuration 33. In the version of FIGS. 1 and 2, the constraint 30 unwraps from a proximal end 17 toward a distal end 18 of a distal support segment 12 of the underlying catheter 11 when changing from the wrapped configuration 31 to the unwrapped configuration 33. Adjacent coils 37 may abut one another or may be slightly spaced apart without departing from the present disclosure. For instance, adjacent coils 37 may have a spacing between themselves that is less than a width dimension of strip 34, but greater spacing could also fall within the intended scope of the present disclosure.

FIGS. 1 and 2 are also of interest for showing a wrapping structure that causes the constraint 30 to unwrap starting at the proximal most coil 37 and unwrapping from a radially inward layer 45 toward a radial outer layer 46, with each subsequent coil being identically wrapped so that they also unwrap from a radially inward toward a radially outward layer. Alternatively, each adjacent coil 37 could alternate in wrapping radially inward to outward to radially outward to inward without departing from the present disclosure. In order to facilitate the unwrapping procedure, the first to unwrap end of the strip 34 may be attached to a control line 50 that extends all the way to a proximal end (not shown) of the stent delivery system 10 to allow a clinician to apply tension to the control line to facilitate the unwrapping procedure. Control line 50 may be a wire formed of a different material, including metallic, or may be identical to strip 34 without departing from the present disclosure. FIGS. 1 and 2 show a configuration in which the strip 34 moves in a proximal direction 19 along axis 14 when the constraint 30 is being changed from the wrapped configuration 31 toward the unwrapped configuration 33. As best shown in FIG. 2, the self expanding stent 20 is in contact with, and held in a compressed state 21 by, the constraint 30 in the wrapped configuration 31, and the stent 20 is in an expanded state 22 out of contact with the constraint 30 while bearing against the blood vessel wall in the unwrapped configuration 33. As used in this disclosure, the term "stent" is inclusive of stent grafts, which typically include a fabric cover.

Figure 3:
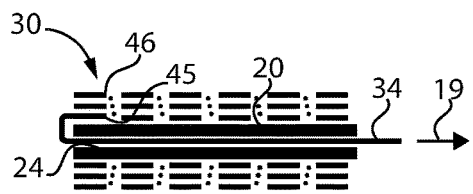
FIGS. 3-10 show constraint winding configurations according to different aspects of the present disclosure.

Referring now in addition to FIGS. 3-10. The constraint 30 may have strip 34 wrapped in a variety of different ways in order to facilitate different action during the unwrapping procedure. FIG. 3 shows a version similar to that of FIGS.

Figure 4:
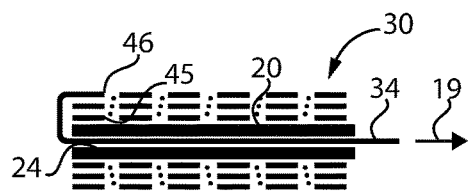
Figure 5:
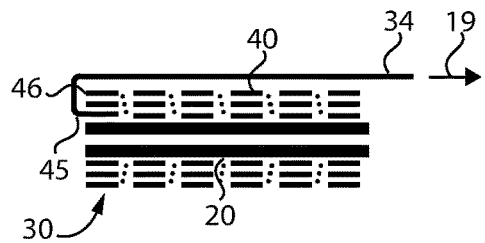
Figure 6:
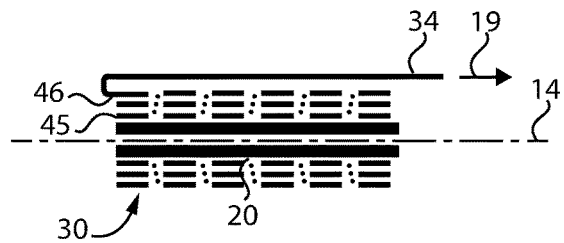
Figure 7:
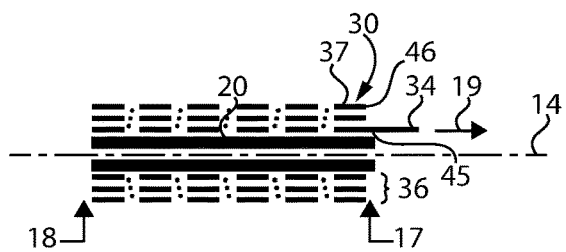
Figure 8:
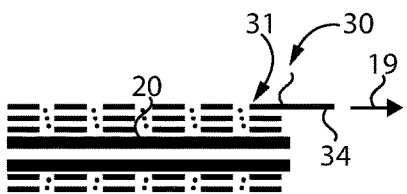
Figure 9:
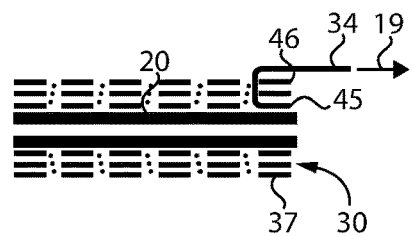
Figure 10:
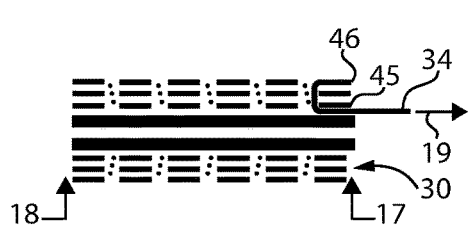

1 and 2 except that the coils sequentially unwrap from a distal most coil to a proximal most coil, which is opposite from that of the embodiment of FIGS. 1 and 2. In addition, the strip 34 moves in a proximal direction 19 along axis 14 through the stent 20 responsive to the constraint 30 changing from the wrapped configuration 31 toward the unwrapped configuration 33. FIG. 4 shows a version similar to that of FIG. 3 except that the strip 34 unwraps from a radial outward layer 46 toward a radially inward layer 45. FIG. 5 shows a version similar to FIG. 3 except that the strip 34 moves along an outer surface 40 of constraint 30 during the unwrapping procedure, as opposed to through stent 20 as in the versions of FIGS. 3 and 4. FIG. 6 is similar to FIG. 5 except that the strip 34 unwraps from a radially outward layer 46 inward toward a radial inward layer 45, but is otherwise identical that of FIG. 5. FIG. 7 shows a constraint structure for unwrapping identical to that of FIGS. 1 and 2. FIG. 8 shows an embodiment similar to FIG. 7 except that the strip 34 unwraps from the radial outward layer 46 first toward the radial inward layer 45. FIG. 9 is of interest for showing the strip moving between adjacent coils while unwrapping from a radially inward layer 45 toward a radially outward layer 46. FIG. 10 is similar to FIG. 9 except that the strip 34 unwraps from the radial outward layer 46 first toward the radial inward layer 45. It is conceivable that each successive coil 37 in a constraint 30 according to the present disclosure could have different wrapping and unwrapping configurations without departing from the present disclosure. The strategies of FIGS. 3 and 4 may be more desirable as these strategies may present a lower risk of entanglement between the strip 34 and the expanding stent 20 during the deployment procedure.

Figure 11:
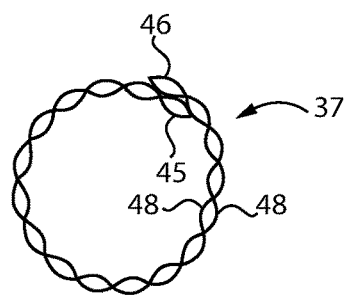
FIG. 11 is an end view showing strip with corrugated surface modifications wrapped onto itself according to the present disclosure.
Figure 12:
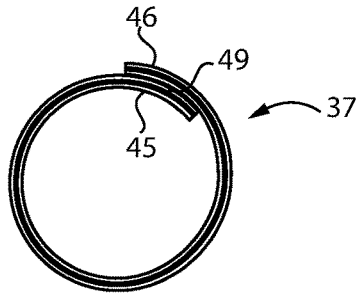
FIG. 12 is an end view showing one coil wrapping using a strip that includes a sticky surface modification.

FIGS. 11 and 12 are of interest for showing that the strip 34 may or may not include surface features that interact when the strip is wrapped onto itself in a coil 37 as shown in the previous embodiments. For instance, FIG. 11 shows that the strip 34 may have a corrugated surface feature 48 as a way of inhibiting the strip 34 from sliding on itself when wrapped onto itself as a coil 37. FIG. 12 is of interest for showing an alternative strategy in which a sticky surface modification 49 to strip 34 also inhibits sliding of the strip over itself. Nevertheless, strip 34 may be made of a slippery material, such as PTFE, with smooth contact surfaces that actually encourages sliding. Thus, the present disclosure contemplates different surface strategies for the strip 34 to inhibit or possibly encourage relative sliding of the strip over itself to better facilitate a deployment procedure. The present disclosure also contemplates constraints 30 that unwrap from a distal end 18 toward a proximal end 17 (FIGS. 3-6), or constraints 30 that unwrap from a proximal end 17 toward a distal end 18 as shown in FIGS. 1, 2 and 7-10. Nevertheless, those skilled in the art will appreciate that wrapping structures that unwrap from a middle position outward could also fall within the intended scope of the present disclosure. The present disclosure also contemplates strategies in which the strip 34 moves in contact with an outer surface 40 of the constraint 30 during the unwrapping procedure as shown for instance in FIGS. 5 and 6, and also versions in which the wrap moves through the stent 20 during the unwrapping procedure as shown in FIGS. 3 and 4.

Figure 13:
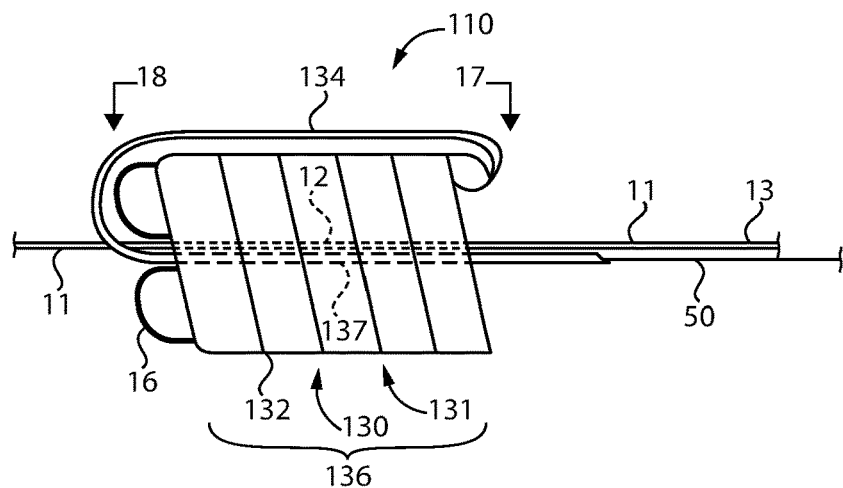
FIG. 13 is a schematic view of a stent deployment system according to another aspect of the present disclosure.
Figure 14:
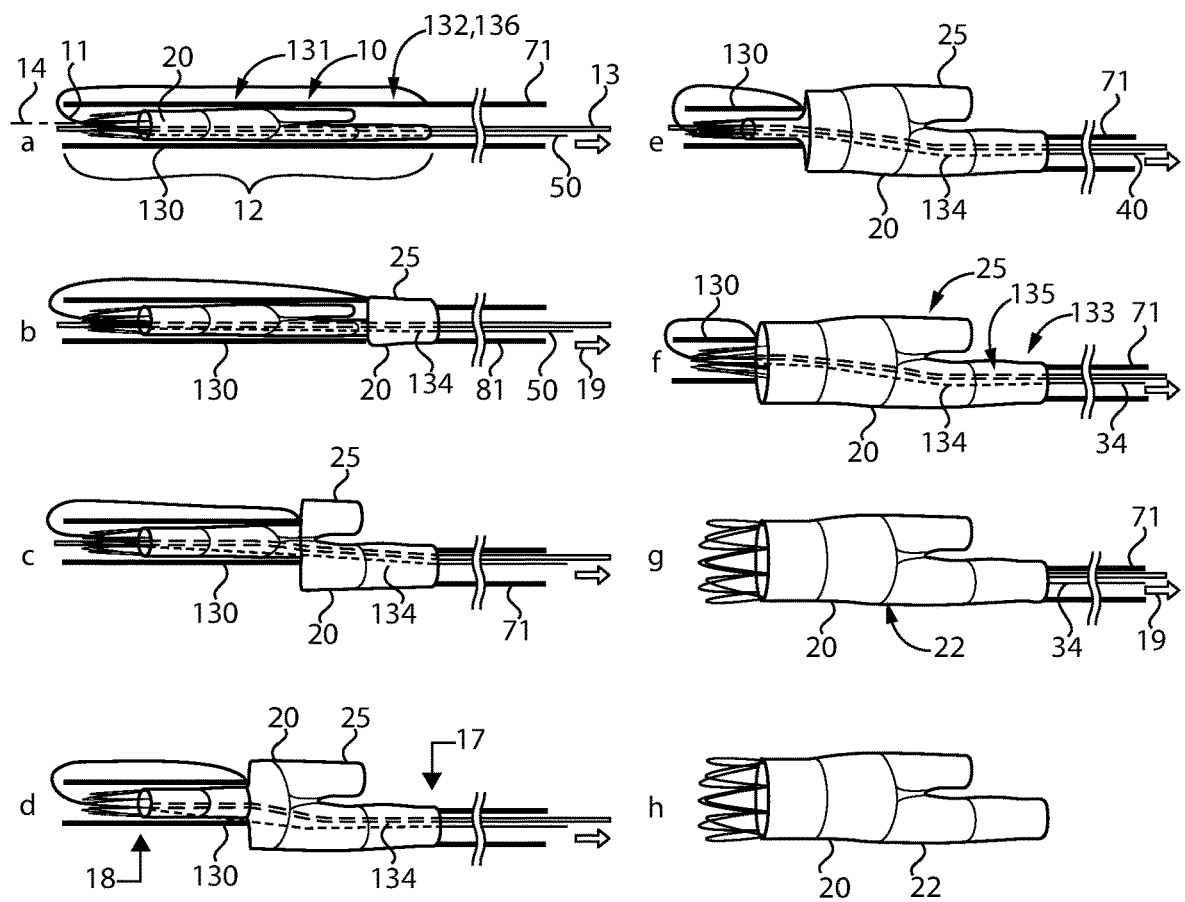
FIG. 14 is a sequence of views showing the stent deployment system of FIG. 13 deploying a stent graft.

Referring now to FIGS. 13 and 14, a stent delivery system 110 includes a constraint 130 that has a wrapped configuration 131, which has a hollow elongated shape 132, and an unwrapped configuration 133, which is a continuous length 135 of a strip 134. This embodiment is similar to the earlier embodiment in that the constraint 130 defines a hollow elongated shape, but except now in the form of a hollow elongated cylinder 136 that includes a helical shape in the wrapped configuration 131. This embodiment differs from the earlier embodiment in that there may only be a single layer of wrap 134 at each axial location along axis 14. For instance, constraint 130 may start out as a hollow cylindrical thin walled tube, and then be weakened along a tear line 76 that has a helical shape. The tear line 76 may be constructed in any manner suitable in the art including UV weakening, mechanically scoring a groove, by creating perforations along tear line 76 or any other manner known in the art to facilitate a tearing unwrapping action in a controllable fashion along helical tear line 76. In all versions of this embodiment, the constraint 130 unwraps from a proximal end 17 toward a distal end 18 of the distal support segment 12 of the underlying catheter 11 when changing from the wrapped configuration 131 toward the unwrapped configuration 133. Unlike the embodiments shown in FIGS. 1-12, the embodiments of FIGS. 13-14 all are constructed in a way that the strip 134 moves in a proximal direction 19 along axis 14 through stent 20 responsive to the constraint 130 changing from the wrapped configuration 131 toward the unwrapped configuration 133. Although not necessary, a funnel component 16 may be included to help in the routing of the strip 134 traveling radially inward to be routed through stent 20. In addition to this strip 134 moving through the stent 20 during the unwrapping procedure, a different portion of the strip 134 initially moves along in a distal direction along axis 14 in contact with an outer surface 40 of a still wrapped portion of the constraint 130 when changing from the wrapped configuration 131 to the unwrapped configuration 133. FIG. 14 is of interest for showing a structure similar to that of FIG. 13 with the stent deployment system delivering an aortic aneurism repair stent graft 20 in an unwrapping procedure in which the constraint 130 unwraps starting at the proximal end 17 and progresses toward the distal end 18 while the strip 134 initially moves along an outer surface 40 of the stent graft 20 and then a portion of 137 moves through the interior 24 stent graft 20 on its way toward the proximal end of the stent delivery system 110 during the deployment unwrapping procedure.

Figure 15:
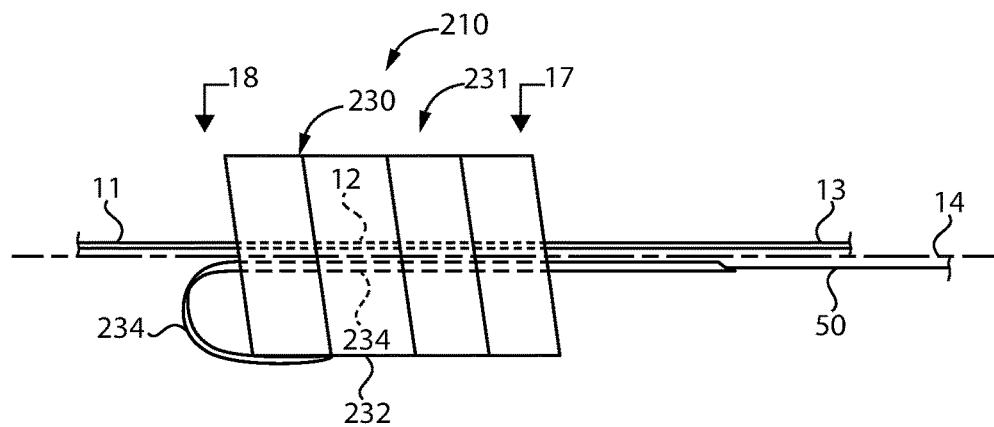
FIG. 15 is a side schematic view of a stent deployment system according to still another aspect of the present disclosure.

Referring now to FIG. 15, a stent deployment system 210 according to still another embodiment according to the present disclosure includes a constraint 230 that unwraps from a distal end 18 toward a proximal end 17 when changing from a wrapped configuration 231 toward an unwrapped configuration. The strip 234 moves in a proximal direction 19 when the constraint 230 changes from the wrapped configuration 231 to the unwrapped configuration. In the embodiment shown, the strip 234 moves within stent 20 during the unwrapping procedure. Nevertheless, those skilled in the art will appreciate that the strip 234 could instead move along an outer surface of an unwrapped portion of the constraint 230 when unwrapping without departing from the present disclosure.

Figure 16:
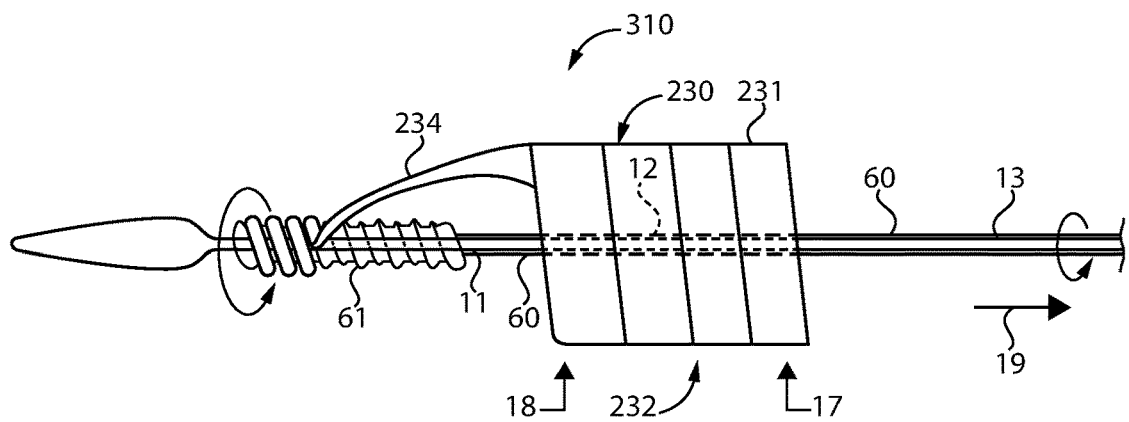
FIG. 16 is a side schematic view of a stent deployment system according to still another aspect of the present disclosure.

Referring now to FIG. 16, a stent deployment system 310 according to still another version of the present disclosure shows constraint 230 unwrapping from a distal end toward a proximal end as in the previous embodiment, but instead of the strip 234 moving toward the proximal end of the delivery device 310, the strip is spooled and counter wound onto a grooved spool 61 of an outer cannula 60. Instead of applying tension to a control line attached to one end of the strip, this deployment teaches unwrapping from the wrapped configuration 231 to the unwrapping configuration 233 by relative rotation of the outer cannula 60 and its spool 61 relative to the constraint 230. The spool 61 could be located proximal from the constraint 230 without departing from the present disclosure. Thus in the embodiment shown, the strip 234 is wound about catheter 11 distal to the stent 20 in the unwrapped configuration 233.

Figures 17, 18:
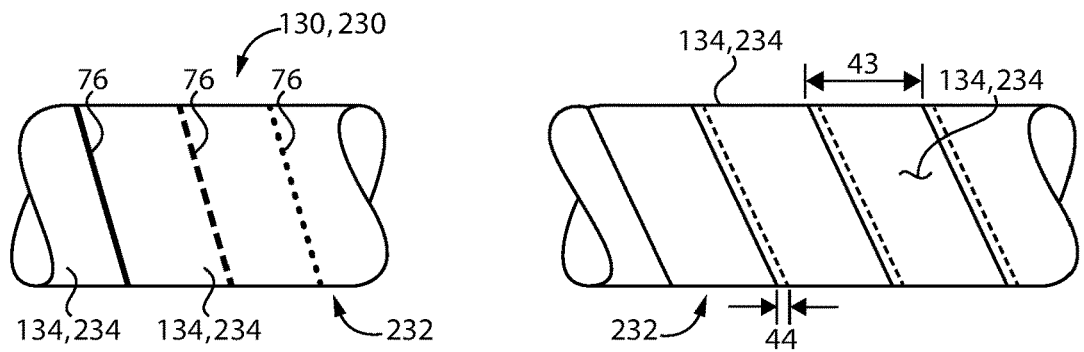
FIG. 17 is a schematic side view showing different strategies for constructing a constraint according to the present disclosure using a tear line.
FIG. 18 is a side schematic view of an overlap strategy for constructing a constraint according to another aspect of the present disclosure.

Referring now to FIGS. 17 and 18, all of the embodiments from FIGS. 13-16 can be constructed in a variety ways. For instance, the constraint 130, 230 may initially be a thin walled tube that is then transformed by creating a helical tear line 76 such as by UV exposure 72, by mechanically creating a dashed perforation line 71, a dotted perforation line 74, or any other weakening material strategy to facilitate tearing along tear line 76 known in the art. In these examples, there will be no overlap in the strip 134, 234 onto itself. Alternatively, as shown in FIG. 18, the strip may be initially a strip 134, 234 and then wound partially onto itself so less than a complete width 43 of the strip overlaps 44 onto itself in the wrapped configuration. Some adhesive may be used in the overlapping area to help hold the constraint in a hollow cylindrical shape prior to unwrapping and deployment. This adhesive attachment along the strip overlap 44 should be sufficiently strong to hold the constraint in a hollow elongated shape 132, 232 prior to deployment, but readily permit detachment along the helical overlap line to facilitate unwrapping during the deployment procedure.

INDUSTRIAL APPLICABILITY

The present disclosure finds potential application in any stent delivery system. The present disclosure finds particular applicability where precise placement and controlled deployment are needed for desirable outcomes. Finally, the present disclosure find specific application in the delivery of stent grafts, especially in cases involving aortic intervention.

Referring to FIG. 2, a method of deploying a stent utilizing a stent delivery system 10 according to the present disclosure is illustrated. The stent delivery system according to the present disclosure may be introduced into a patient's body in a conventional manner and be maneuvered to an implantation site, such as by utilizing a wire guide, in a known manner that need not be taught again here. FIG. 2a shows the stent delivery system after it has been positioned at a delivery site, but before the constrained stent 20 has been deployed. After the clinician confirms that the stent delivery system is properly positioned by utilizing appropriate imaging and other techniques, deployment is initiated by applying tension to control line 50 from a proximal end (not shown) of the stent delivery system 10 that is positioned outside of the patient's body. As the control line 50 is pulled in proximal direction 19, the first coil 37 begins to unwrap to allow stent 20 to assume a partially expanded state 25. As the deployment continues, the strip 34 continues to unwrap and moves along an external surface 23 of stent 20 as shown in FIGS. 2b and 2c. Eventually, the constraint 30 is completely unwrapped and arrives at its unwrapped configuration 33 with the continuous length 35 of strip 34 out of contact with stent 20, which now has achieved its expanded state 22 at the desired deployment location. Those skilled in the art will appreciate that, a stent deployment system according to a different embodiment (e.g., FIG. 16) may be deployed by unwrapping the constraint via relative rotation to take up the strip on a spool positioned either proximally or distally from stent 20.

The present disclosure may significantly reduce deployment forces/friction, which may improve the clinician's experience and also prevent accidental device movement or dislodging during deployment, which has sometimes been a problem in the prior art. Furthermore, the initial positioning of the stent may be maintained during the deployment procedure. In addition, the unwrapping strategy provides for a controlled partial deployment of the stent which may permit some repositioning during the deployment procedure. Depending upon the wrapping strategy, deployment may begin at a proximal end, in the middle or at a distal end of the underlying stent to further add in accurate placement. In addition, the wrapping strategy may permit an overall profile reduction by allowing a constraint with a lower profile than retractable sheaths associated with the prior art. In addition, it is believed that the unwrapping strategy may reduce or eliminate the impact of blood flow on a stent graft during deployment to help avoid undesirable folding in the stent graft material. The present disclosure might also facilitate the use of simpler materials and possibly eliminate separate DRT structures. Finally, materials for constructing a constraint according to the present disclosure may be selected from existing medical materials already approved for stent delivery systems.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. A stent delivery system comprising:
 a catheter having an axis, a distal support segment and a proximal segment;
 a self-expanding stent positioned about the distal support segment;
 a constraint having a wrapped configuration, which has a hollow elongated shape, and an unwrapped configuration, which is a continuous length of a strip;
 wherein the stent is in contact with, and held in a compressed state by, the constraint in the wrapped configuration, and the stent is in an expanded state out of contact with the constraint in the unwrapped configuration;
 wherein the constraint unwraps from a proximal end toward a distal end of the distal support segment when changing from the wrapped configuration to the unwrapped configuration; and
 wherein a portion of the strip moves in a proximal direction along the axis through the stent responsive to the constraint changing from the wrapped configuration toward the unwrapped configuration.

2. The stent delivery system of claim 1 wherein the constraint defines a hollow elongated cylinder that includes a helical shape in the unwrapped configuration.

3. The stent delivery system of claim 1 wherein less than a complete width of the strip overlaps, and is parallely oriented with, itself in the wrapped configuration.

4. The stent delivery system of claim 1 wherein a portion of the strip moves in a distal direction along the axis in contact with an outer surface of a wrapped portion of the constraint responsive to the constraint changing from the wrapped configuration toward the unwrapped configuration.

5. The stent delivery system of claim 1 wherein the constraint changes from the wrapped configuration toward the unwrapped configuration responsive to rotation of the catheter about the axis relative to the constraint.

6. The stent delivery system of claim 5 wherein the strip is wound about the catheter distal to the stent in the unwrapped configuration.

\* \* \* \* \*